United States Patent [19]

Strong

[11] Patent Number: 5,410,062

[45] Date of Patent: Apr. 25, 1995

[54] PREPARATION OF SUBSTITUTED-2,3-DICARBOXYPYRIDINIUM NITRATES

[75] Inventor: Henry L. Strong, Somerset, N.J.

[73] Assignee: American Cyanamid Company, Wayne, N.J.

[21] Appl. No.: 190,825

[22] Filed: Feb. 2, 1994

Related U.S. Application Data

[62] Division of Ser. No. 967,349, Oct. 28, 1992, Pat. No. 5,284,955.

[51] Int. Cl.$^6$ .......................................... C07D 213/807
[52] U.S. Cl. .................................. 546/170; 546/320; 546/321
[58] Field of Search ............... 546/347, 170, 321, 322, 546/320

[56] References Cited

U.S. PATENT DOCUMENTS

| | | | |
|---|---|---|---|
| 4,316,026 | 2/1982 | Hatano et al. | 546/5 |
| 4,798,619 | 1/1989 | Los | 504/156 |
| 5,122,608 | 6/1992 | Strong | 546/170 |

OTHER PUBLICATIONS

Mullock et al., *J. Chem. Society*, Section C, Part I, pp. 829–833, 1970.
Merck Index, ONR–84, 1983.
Chemical Abstracts, vol. 68, No. 7, Abstract No. 39,436a, p. 3827, Feb. 12, 1968.
Chemical Abstracts, vol. 93, No. 9, Abstract No. 103,747y, p. 552, Sep. 1, 1980.
Chemical Abstracts, vol. 107, No. 7, Abstract No. 59,689n Aug. 17, 1987.
A. Dornow, W. Schact 'Ueber die Darstellung des Chem. Ber. vol. 80, No. 6, 1947 pp. 505–509.
P. Sutter and C. Weis, Journal of Heterocyclic Chemistry, 23 pp. 29–32 (1986).
Chemical Abstracts, vol. 112, No. 9 Abstract 76,991a, p. 783, Feb. 26, 1990.

Primary Examiner—Bernard Dentz
Assistant Examiner—Zinna N. Davis
Attorney, Agent, or Firm—John W. Hogan, Jr.

[57] ABSTRACT

There are provided crystalline substituted-2,3-dicarboxypyridinium nitrate salts, the preparation thereof and the use thereof in the isolation and purification of important substituted pyridinedicarboxylic acid herbicide intermediates.

8 Claims, No Drawings

PREPARATION OF SUBSTITUTED-2,3-DICARBOXYPYRIDINIUM NITRATES

This is a divisional of co-pending application, Ser. No. 07/967,349, filed on Oct. 28, 1992 now U.S. Pat. No. 5,284,955.

BACKGROUND OF THE INVENTION

Substituted 2,3-pyridinedicarboxylic acids are important intermediates in the manufacture of highly effective 2-(2-imidazolin-2-yl)nicotinate herbicides. Among the methods to prepare substituted 2,3-pyridinedicarboxylic acids is the nitric acid oxidation of the appropriately substituted quinoline precursor. However, certain substituted pyridinedicarboxylic acids are difficult to isolate from the spent nitric acid solution. Such compounds do not readily precipitate from the product solution.

The compound, 2,3-dicarboxypyridinium nitrate is described by P. Sutter and C. Weis in the Journal of Heterocyclic Chemistry, 23 p. 29–32 (1986), however no substituted 2,3-dicarboxypyridinium nitrates are found therein.

Therefore, it is an object of this invention to provide crystalline substituted 2,3-dicarboxypyridinium nitrate compounds which are useful in the isolation and purification of important 2,3-pyridinedicarboxylic acid herbicide intermediates. It is another object of this invention to provide a means for producing the desired substituted pyridinedicarboxylic acid herbicide intermediates in improved yield and purity.

It is a feature of this invention that the desired dicarboxylic acid product may be obtained without necessitating a quenching step, thereby allowing the spent nitric acid to be recycled and eliminating the costly and potentially hazardous presence of solvent wastes.

SUMMARY OF THE INVENTION

The present invention provides a substituted 2,3-dicarboxypyridinium nitrate compound of formula I

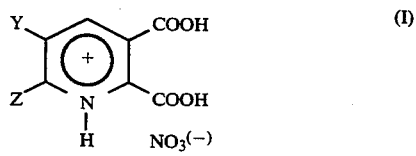

wherein Y and Z are each independently hydrogen, $C_1$-$C_6$alkyl optionally substituted with one or more $C_1$-$C_4$ alkoxy, halogen or sulfonyl groups, nitro, formyl, $C_1$-$C_4$ alkylcarbonyl, $C_1$-$C_4$ alkylsulfonyl or phenyl optionally substituted with $C_1$-$C_4$ alkyl, $C_1$-$C_4$ alkylsulfonyl, halogen, or haloalkyl groups
with the proviso that one of Y or Z must be other than hydrogen,
or when taken together Y and Z may form a ring wherein YZ is represented by the structure

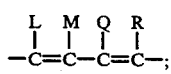

L, M, q and R are each independently hydrogen, $C_1$-$C_4$ alkyl, $C_1$-$C_4$ alkoxy, $C_1$-$C_4$ alkylsulfonyl, $C_1$-$C_4$ haloalkyl, nitro, phenyl optionally substituted with one $C_1$-$C_4$ alkyl or halogen group or phenoxy optionally substituted with one halogen, $C_1$-$C_4$ alkyl, nitro or $CF_3$ group with the proviso that only one of L, M, Q or R may represent a substituent other than hydrogen, halogen, $C_1$-$C_4$ alkyl or $C_1$-$C_4$ alkoxy.

The invention further provides a method for the preparation of a formula I pyridinium nitrate compound which comprises reacting a substituted quinoline compound of formula II

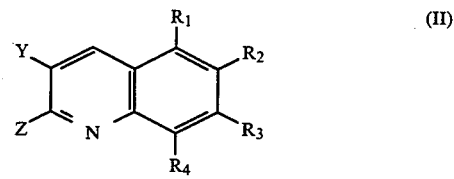

wherein Y and Z are as described for formula I above and $R_1$, $R_2$, $R_3$ and $R_4$ are each independently hydrogen, (II) hydroxy, nitro, amino, $SO_3H$ or $SO_3Cl$ with the proviso that one of $R_1$, $R_2$, $R_3$ or $R_4$ is other than hydrogen; with nitric acid optionally in the presence of a catalytic amount of Manganese and a nitroaromatic solvent, at an elevated temperature to form a reaction mixture and concentrating the reaction mixture to give the crystalline formula I compound.

The formula I dicarboxypyridinium nitrate is readily converted to the corresponding pyridinedicarboxylic acid upon treatment with a solvent or solvent mixture. The thus-obtained, high purity pyridinedicarboxylic acid is an important intermediate in the production of 2-(2-imidazolin-2-yl)nicotinate herbicidal agents. Descriptions of these highly effective herbicidal agents and the use of substituted 2,3-pyridinedicarboxylic acid in their preparation can be found in U.S. Pat. No. 4,798,619 among others.

A method to prepare substituted 2,3-pyridinedicarboxylic acid via the nitric acid oxidation of the appropriate quinoline precursor in the presence of a Manganese catalyst is described in co-pending patent application Ser. No. 07/967,350, filed Oct. 28, 1992 and incorporated herein by reference thereto.

DETAILED DESCRIPTION OF THE INVENTION

The Skraup reaction is a well-known and convenient source of the formula II substituted quinoline starting material used in the manufacture of substituted 2,3-pyridinedicarboxylic acid herbicide intermediates. The Skraup reaction is carried out in an aqueous acidic solution. Advantageously, it has now been found that crude Skraup reaction mixtures, without undue and tedious isolation procedures, may be used as a source of starting material in the nitric acid oxidation of formula II quinoline compounds to produce high purity substituted 2,3-pyridinedicarboxylic acid products. Surprisingly, it has been found that concentration of the spent nitric acid solution in the presence of a nitroaromatic solvent such as nitrobenzene or nitroxylenes yields a crystalline nitrate salt of formula I in high yield. The formula I dicarboxypyridinium nitrate is easily converted to the desired 2,3-pyridinedicarboxylic acid upon treatment with a second solvent or solvent mixture. The desired oxidation product is thus obtained without the need to quench the reaction solution and thereby allowing for the recyclization of the spent nitric acid. The procedure is illustrated in Flow Diagram I.

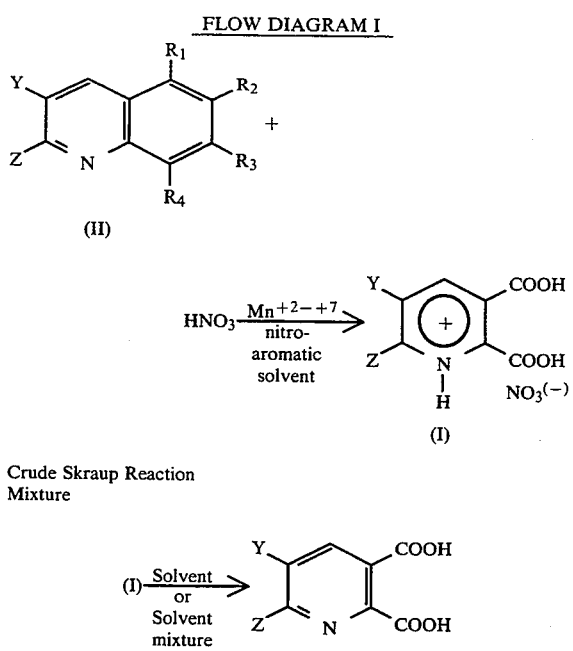

Crude Skraup Reaction Mixture

The formula I dicarboxypyridinium nitrate compounds of the invention allow the isolation and purification of important herbicide intermediate compounds. Many of the desired 2,3-pyridinedicarboxylic acid compounds are difficult to isolate from the spent nitric acid solution resulting from the oxidation procedure. Even after quenching the nitric acid with reagents such as formic acid or isopropanol and/or adjusting the pH of the reaction mixture, certain substituted pyridinedicarboxylic acids (e.g. 5-ethyl pyridinedicarboxylic acid) do not readily precipitate from solution. High concentration of the quenched nitric acid product solution results in exotherms, product decomposition, $NO_x$ gas emission and potentially explosive mixtures. Surprisingly, the substituted pyridinedicarboxylic acid compound crystallizes from solution as the pure nitric acid addition salt in high yield when the spent nitric acid oxidation reaction solution is concentrated in the presence of a nitroaromatic solvent such as nitrobenzene or nitroxylenes such as 3-nitro-o-xylene. Therefore, the presence of costly and potentially hazardous solvent wastes are eliminated.

In actual practice, a formula II quinoline compound, either isolated or present as a crude reaction product solution, optionally in the presence of a solvent, is added to a mixture of 70% nitric acid and a catalytic amount of Manganese at a temperature range of about 50°–150° C. to form a reaction mixture, the reaction mixture is heated at 50°–150° C. until the oxidation is complete. The unquenched reaction mixture is treated directly with a nitroaromatic solvent such as nitrobenzene, 3-nitro-o-xylene and the like and concentrated in vacuo to give the formula I dicarboxypyridinium nitrate compound as a crystalline precipitate. The pyridinium nitrate precipitate is isolated by filtration and converted to the corresponding free 2,3-pyridinedicarboxylic acid by treatment with a second solvent or solvent system. Suitable solvents for the conversion of the formula I dicarboxypyridinium nitrate to the corresponding 2,3-pyridinedicarboxylic acid are ketones such as methyl isobutyl ketone, acetone and the like, mixtures of a ketone and a halogenated hydrocarbon such as methylene chloride, chloroform, ethylene dichloride and the like and water and mixtures of water and a co-solvent such as a ketone or halogenated hydrocarbon. Treatment of the formula I pyridinium nitrate compound of the invention with a suitable solvent or solvent mixture yields the desired substituted 2,3-pyridinedicarboxylic acid in good yield and high purity.

The invention herein described is further illustrated by the following Examples and is not to be deemed limited thereby except as defined in the claims. Unless otherwise, noted all parts are parts by weight. The term HPLC designates high performance liquid chromatography.

EXAMPLE 1

Preparation of 2,3-dicarboxy-5-ethylpyridinium nitrate

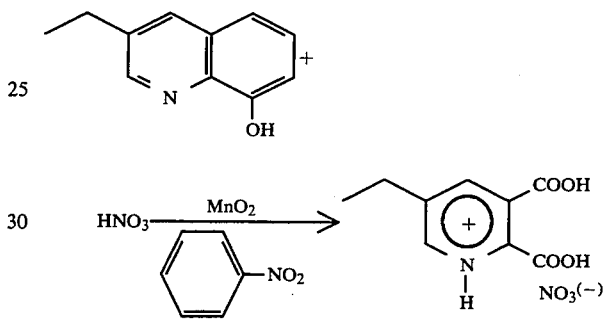

A mixture of 70% nitric acid (480 g, 5.33 mole) and manganese dioxide (0.1 g, 1.75 mmole) is heated to 95° C., treated with a solution of 3-ethyl-8hydroxyquinoline (51.5 g, 67.5% pure, 0.20 mole) in 100 g nitrobenzene over a 2 hour period, held at 90°–100° C. for 10 hours, cooled to room temperature, treated with an additional 200 g of nitrobenzene, concentrated in vacuo to a total weight of about 240 g and filtered. The filter cake is washed with nitrobenzene and methylene chloride and dried in vacuo to give the title product as a white solid, 49.2 g (95.3% yield), mp 109°–111° C. The product is used as is in Example 2.

EXAMPLE 2

Preparation of 5-ethyl-2,3-pyridinedicarboxylic acid

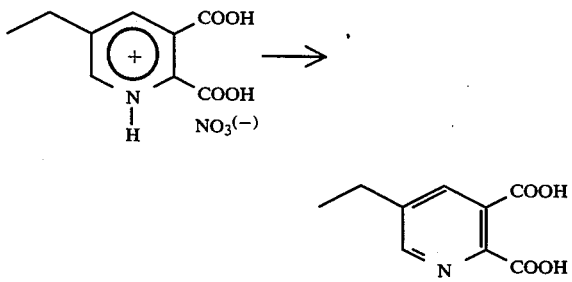

The nitrate salt obtained in Example 1 is dispersed in a mixture of 100 mL of methylene chloride and 100 mL of methyl isobutyl ketone, heated at reflux temperature for 1 hour, cooled to room temperature and filtered. The filter cake is washed with a 1:1 mixture of methylene chloride:methyl isobutyl ketone and dried in vacuo to give 5-ethyl-2,3-pyridinedicarboxylic acid, 34.6 g, (89% isolated yield from 3-ethyl-8-hydroxyquinoline), 94.5% pure by HPLC.

EXAMPLE 3

Preparation of substituted 2,3-dicarboxypyridinium nitrate

Using essentially the same procedure described in Example 1 and employing the appropropriate substituted quinoline precursor, the following dicarboxypyridinium nitrate compounds are obtained:

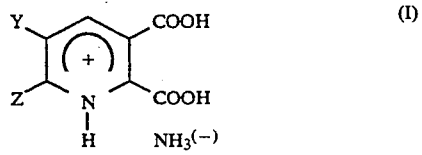

| Y | Z | mp °C. |
|---|---|---|
| $CH_3$ | H | 167–168 |
| H | H | 155–158 |
| $CH_2OCH_3$ | H | 92–94 |

EXAMPLE 4

Preparation of 5-ethyl-2,3-pyridinedicarboxylic acid in high purity from crude 3-ethyl-8-hydroquinoline starting material via the isolation of 2,3-dicarboxy-5-ethylpyridinium nitrate

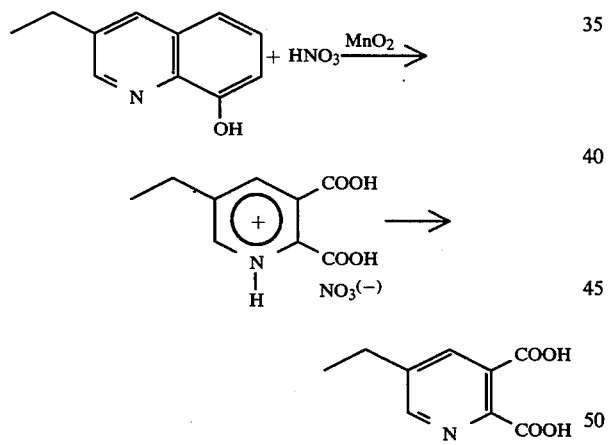

A mixture of 70% nitric acid and a catalytic amount of maganaese dioxide is treated with a solution of crude (67.5% pure) 3-ethyl-8-hydroxyquinoline (EHQ) in nitrobenzene (NBz) or 3-nitro-9-xylene (3-NOX) at 95° C., heated at 90°–100° C. until oxidation is complete, cooled to room temperature, concentrated in vacuo in the presence of the nitroaromatic solvent and filtered to give 2,3-dicarboxy-5-ethylpyridinium nitrate. The thus-isolated nitrate salt is dispersed in a 1:1 mixture of methylene chloride ($CH_2C_{12}$) and methyl isobutyl ketone (MIBK) or acetone and $CH_2C_{12}$ and filtered to give the desired 5-ethyl-2,3-pyridinedicarboxylic acid in high purity.

Varying the above reaction parameters and the solvent systems used to liberate the free pyridinedicarboxylic acid compound from the isolated dicarbox-ypyridinium nitrate, the following results are obtained and shown in Table I.

TABLE I

Preparation of 5-Ethyl-2,3-pyridinedicarboxylic Acid

| Molar Ratio $HNO_3$:EHQ | $HNO_3$ Oxid'n Solvent | Nitrate Salt Dispersant | % Yield from EHQ | % Purity |
|---|---|---|---|---|
| 16 | 3-NOX | 3-NOX/HCOOH | 83.3 | 78.1 |
| 16 | 3-NOX | 3-NOX/HCOOH | 84.2 | 78.2 |
| 16 | NBz | MIBK | 74.9 | 98.0 |
| 16 | 3-NOX | MIBK | 75.7 | 93.5 |
| 16 | NBz | MIBK/HCOOH | 73.0 | 96.3 |
| 16 | 3-NOX | MIBK/HCOOH | 78.5 | 94.4 |
| 16 | 3-NOX | MIBK/HCOOH* | 83.8 | 95.4 |
| 16 | 3-NOX | MIBK/$CH_2Cl_2$ | 86.2 | 91.9 |
| 16 | 3-NOX | MIBK/$CH_2Cl_2$ | 90.5 | 91.4 |
| 16 | 3-NOX | MIBK/$CH_2Cl_2$ | 80.4 | 93.1 |
| 18 | 3-NOX | MIBK/$CH_2Cl_2$ | 80.6 | 90.9 |
| 18 | NBz | MIBK/$CH_2Cl_2$ | 83.8 | 94.5 |
| 18** | NBz | MIBK/$CH_2Cl_2$ | 55.4 | 91.2 |
| 16 | 3-NOX | Acetone | 72.1 | 97.7 |
| 16 | 3-NOX | Acetone/$CH_2Cl_2$ | 67.8 | 96.5 |
| 18 | 3-NOX | Acetone/$CH_2Cl_2$ | 64.4 | 97.3 |

*Water extraction
**Starting material was not isolated from Skraup reaction mixture

I claim:
1. A method for the preparation of a compound of formula I

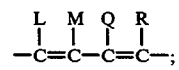

(I)

wherein Y and Z are each independently hydrogen,
  $C_1$-$C_6$ alkyl optionally substired with one or more $C_1$-$C_4$ alkoxy, halogen or sulfonyl groups, nitro, $C_1$-$C_4$ alkylcarbonyl, $C_1$-$C_4$ alkylsulfonyl or phenyl optionally substituted with
  $C_1$-$C_4$ alkyl, $C_1$-$C_4$ alkylsulfonyl, halogen, or haloalkyl groups
with the proviso that one of Y or Z must be other than hydrogen,
or when taken together Y and Z may form a ring wherein YZ is represented by the structure $$\begin{array}{cccc} L & M & Q & R \\ | & | & | & | \\ -C & = C & - C & = C-; \end{array}$$

L, M, Q and R are each independently hydrogen, $C_1$-$C_4$ alkyl, $C_1$-$C_4$ alkoxy, $C_1$-$C_4$ alkylsulfonyl, $C_1$-$C_4$ haloalkyl, nitro, phenyl optionally substituted with one $C_1$-$C_4$ alkyl or halogen group or phenoxy optionally substituted with one halogen, $C_1$-$C_4$ alkyl, nitro or $CF_3$group with the proviso that only one of L, M, Q or R may represent a substituent other than hydrogen,halogen, $C_1$-$C_4$ alkyl or $C_1$-$C_4$ alkoxy which comprises reacting a compound of formula II

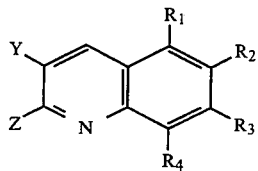

(II)

wherein Y and Z are described for formula I above and $R_1$, $R_2$, $R_3$ and $R_4$ are each independently hydrogen, hydroxy, nitro, amino, $SO_3H$ or $SO_3Cl$ with the proviso that at least one of $R_1$, $R_2$, $R_3$ and $R_4$ is other than hydrogen; with nitric acid optionally in the presence of a catalytic amount of Manganese at an elevated temperature to form a reaction mixture and concentrating the reaction mixture in the presence of a nitroaromatic solvent to give the crystalline formula I compound.

2. The method according to claim 1 wherein the Manganese is present as $KMnO_4$ or $MnO_2$.

3. The method according to claim 1 wherein the nitroaromatic solvent is nitrobenzene.

4. The method according to claim 1 wherein the nitroaromatic solvent is 3-nitro-o-xylene.

5. The method according to claim 1 wherein the elevated temperature is about 50°–150° C.

6. The method according to claim 1 for the preparation of the compound of formula I wherein Y is $C_1$-$C_6$alkyl or hydrogen and Z is hydrogen.

7. The method according to claim 1 for the preparation of the compound of formula I wherein Y is methoxymethyl or halomethyl and Z is hydrogen.

8. The method according to claim 1 wherein the nitroaromatic solvent is part of the reaction mixture.

* * * * *

UNITED STATES PATENT AND TRADEMARK OFFICE
CERTIFICATE OF CORRECTION

PATENT NO. : 5,410,062
DATED : April 25, 1995
INVENTOR(S) : Henry L. Strong

It is certified that error appears in the above-indentified patent and that said Letters Patent is hereby corrected as shown below:

Columns 32-38, claim 1, should read -- " 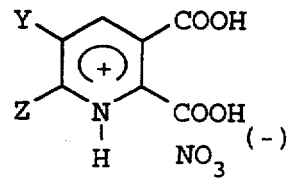 "

(I)

Column 8, line 13, claim 6, should read--"$C_6$alkyl and Z is hydrogen."

Signed and Sealed this

Seventeenth Day of December, 1996

Attest:

BRUCE LEHMAN

Attesting Officer     Commissioner of Patents and Trademarks